United States Patent [19]

Hansford

[11] 4,124,629
[45] Nov. 7, 1978

[54] THERMALLY STABLE COPRECIPITATED CATALYSTS USEFUL FOR METHANATION AND OTHER REACTIONS

[75] Inventor: Rowland C. Hansford, Yorba Linda, Calif.

[73] Assignee: Union Oil Company of California, Los Angeles, Calif.

[21] Appl. No.: 758,042

[22] Filed: Jan. 10, 1977

Related U.S. Application Data

[63] Continuation-in-part of Ser. No. 621,696, Oct. 14, 1975, abandoned, which is a continuation-in-part of Ser. No. 511,187, Oct. 2, 1974, abandoned.

[51] Int. Cl.² ............................ C07C 1/04; C07C 1/10
[52] U.S. Cl. ............................ 260/449.6 M; 252/373; 252/466 J; 252/463; 423/655; 423/656
[58] Field of Search ................... 260/449 M, 449.6 R, 260/449.6 M, 449.6; 252/466 J, 463, 373

[56] References Cited

U.S. PATENT DOCUMENTS

| 1,820,417 | 8/1931 | Williams | 423/362 |
| 1,830,705 | 11/1931 | Marx et al. | 252/463 |
| 2,151,329 | 3/1939 | Page et al. | 260/449 M X |
| 2,898,306 | 8/1959 | Cramer et al. | 252/463 |
| 3,147,227 | 9/1964 | Hansford | 252/317 |
| 3,320,182 | 5/1967 | Taylor et al. | 252/466 |
| 3,361,535 | 1/1968 | Pollitzer et al. | 252/466 J |
| 3,642,460 | 2/1972 | Thompson | 260/449 M |
| 3,709,669 | 1/1973 | Marlon et al. | 260/449 M |
| 3,876,557 | 4/1975 | Bland | 260/449 M X |

Primary Examiner—Howard T. Mars
Attorney, Agent, or Firm—Lannas S. Henderson; Richard C. Hartman; Dean Sandford

[57] ABSTRACT

Catalysts having a high degree of thermal stability, comprising alumina and one or more of the iron group metals are prepared from aqueous solutions containing a dissolved aluminum salt, a salt of at least one of the iron group metals and a delayed precipitant such as urea. The solution is heated to a temperature sufficient to hydrolyze the delayed precipitant with resultant liberation of ammonia and carbon dioxide homogeneously throughout the solution, until the pH of the solution rises sufficiently to effect coprecipitation of the metal salts as hydroxides and/or carbonates. The resulting coprecipitate is then recovered, washed, dried, shaped and calcined in conventional fashion to obtain a final product which, after hydrogen-reduction is very active, and displays much greater thermal stability than corresponding prior art catalysts prepared by non-homogeneous coprecipitation with alkaline, ionic reagents such as sodium carbonate, ammonium hydroxide, or ammonium carbonate. The nickel-containing catalysts are particularly useful for methanation, but they are all useful in a variety of other reactions.

16 Claims, No Drawings

THERMALLY STABLE COPRECIPITATED CATALYSTS USEFUL FOR METHANATION AND OTHER REACTIONS

RELATED APPLICATIONS

This application is a continuation-in-part of Ser. No. 621,696, filed Oct. 14, 1975, now abandoned, which in turn is a continuation-in-part of Ser. No. 511,187, filed Oct. 2, 1974, now abandoned.

BACKGROUND AND SUMMARY OF INVENTION

Catalysts comprising coprecipitated composites of alumina with oxides of one or more of the iron group metals (iron, cobalt and nickel) are very well known in the art. However, conventional methods for preparing such catalysts usually involve adding to an acidic solution of the desired metal salts a highly alkaline ionic precipitant such as ammonium hydroxide, potassium hydroxide, sodium carbonate, etc. This technique always results in non-homogeneous coprecipitation because the respective metal hydroxides precipitate at different instantaneous pH's; the initial distribution of the precipitant in the aqueous medium is non-homogeneous, with the result that precipitation occurs non-homogeneously under widely differing pH conditions throughout the body of the liquid. Under these conditions it is obvious that a uniform coprecipitate of aluminum hydroxide and the active metal hydroxide will not be obtained, and there will not be a high degree of dispersion of the active metal in the coprecipitate. The resulting compositions are generally deficient in thermal stability, due presumably to the tendency of the unbound and heterogeneously distributed active metal to migrate and form larger agglomerates at high temperatures.

It is known (as described for example in my U.S. Pat. No. 3,147,227) that individual hydrous metal oxides and/or phosphates can be precipitated as hydrogels by the slow hydrolysis of urea. This is homogeneous precipitation because the precipitating agent (ammonia) is released slowly and uniformly throughout the body of the solution. However, it would hardly be expected that a uniform coprecipitation of two or more hydrous metal oxides could be obtained by this method because of the large variation in pH at which precipitation of metal hydroxides occur. Thus, zirconium hydroxide begins to precipitate at pH 2.0, aluminum hydroxide at 4.1, nickel hydroxide at 6.7, and magnesium hydroxide at 10.5.

I have now discovered however that a delayed precipitant such as urea, which by hydrolysis liberates ammonia and carbon dioxide uniformly throughout an aqueous medium, can be used to effect a homogeneous coprecipitation of aluminum hydroxide and an incompletely identified basic compound of one or more of the iron group metals when the latter is initially present in solution as a divalent metal salt. This coprecipitation begins to take place at about pH 4.0–4.5, and continues substantially homogeneously until completed at a pH in the range of about 6.0–7.5. The explanation for this phenomenon is not understood completely or with certainty, but it would appear that the ionic divalent metal may precipitate as some form of basic carbonate, beginning at substantially the same pH at which aluminum hydroxide begins to precipitate. X-ray analyses of the coprecipitated, dried nickel-alumina composites have given diffraction patterns very similar, but not identical, to that of basic nickel carbonate, $NiCO_3 \cdot 2Ni(OH)_2 \cdot 4H_2O$.

After drying, calcining, and reducing, the coprecipitated composites are found to display a remarkable degree of thermal stability, as well as high activity in chemical conversions wherein fluid reactants are converted to chemically different products at elevated temperatures under reducing conditions. Surprisingly, these results are obtained even though the surface area of the active metal in the final catalyst is quite low, generally below 18 $m^2/g$, even for catalysts containing as much as 60 weight-percent of active metal oxide.

The foregoing surprising results are not merely the function of a precipitating medium containing both hydroxide and carbonate ions. U.S. Pat. No. 3,320,182 to Taylor et al discloses a coprecipitated nickel-alumina catalyst, employing as the precipitant ammonium bicarbonate. As will be shown hereinafter, catalysts prepared by this method are definitely inferior in thermal stability, compared to the catalysts of this invention.

The remarkable properties of the present catalysts are not however attributable solely to the homogeneous precipitation technique; homogeneous *co*precipitation is required. The urea hydrolysis method can be applied separately to an aluminum salt solution, and to one of the iron group metal salt solutions to obtain homogeneously but separately precipitated components. But upon admixture of these separately precipitated components, the finished catalysts obtained therefrom are found to be much inferior in thermal stability, and the alumina surface area after calcination is very low. It would thus appear that homogeneous coprecipitation from the same solution results in some chemical and/or physical interaction between the two components, which not only produces superior thermal stability, but stabilizes the surface area of the alumina component.

Although it is not possible to account with certainty for the thermal stability of the catalysts of this invention, it is believed attributable at least in part to the presence therein of a "reservoir" of inactive divalent metal-aluminate which during use under reducing conditions slowly generates fresh active metal surface, replacing the active surface area being lost through agglomeration. Electron diffraction studies have detected nickel aluminate crystallites in the nickel-alumina catalysts prepared herein, and its presence could account for the relatively low surface area of active metal found in the freshly reduced catalysts.

DETAILED DESCRIPTION

The operative delayed precipitants for use herein may be defined broadly as any water soluble compound which, when dissolved in the mixed salt solution to be coprecipitated, does not initially raise the pH thereof to above about 4.0, but which upon heating to a higher temperature hydrolyzes to give ammonia and carbon dioxide, thereby raising the pH of the solution to bring about coprecipitation. From the standpoint of economy, urea is by far the preferred precipitant, but other compounds are operative, including materials such as ammonium cyanate, ammonium carbamate, potassium thiocyanate, and the like. The amount of precipitant employed should be at least the stoichiometric amount required to precipitate all salt components, calculated as hydroxides. Preferably a stoichiometric excess amounting to about 10–60% is utilized in order to bring about a more rapid and complete precipitation. The metal salts and precipitant may be dissolved simultaneously, or separate solutions thereof may be prepared and blended with each other. The basic requirement is that all components of the solution should be homogeneously dissolved at a temperature sufficiently low to avoid any significant precipitation prior to reaching homogeneity.

Since all of the water soluble salts of aluminum and the divalent metals, iron, cobalt and nickel, form acidic aqueous solutions, any of such may be employed herein. From the standpoint of economy and ready availability, the nitrates, chlorides, sulfates, formates, acetates and the like are preferred. The salts of monovalent anions are preferred, and especially the nitrates. The ratio of aluminum salt to divalent metal salt in the solution should be such as to provide a coprecipitate which, after calcination, will contain about 5–80%, preferably 10–80% and still more preferably about 15–70% by weight of active metal oxide.

Coprecipitation may be produced in the homogeneous solution either rapidly or slowly, depending upon the rate of heatup, the final temperature attained, and the concentration of precipitant in the solution. At temperatures below 100° C., urea hydrolyzes at a fairly slow rate, normally requiring from about 10–50 hours to bring about complete coprecipitation, if no more than the stoichiometric proportion of urea is utilized. However, by utilizing an excess of urea, and/or by operating at higher temperatures under pressure, precipitation may be considerably hastened, such that completion may be obtained in 2 to 8 hours or less.

If the heat supply to the reacting solution does not provide uniform temperatures throughout, agitation or stirring is recommended, although at temperatures above about 90° C. at atmospheric pressure, there is a rapid evolution of carbon dioxide which itself provides considerable agitation. Preferred operating temperatures range between about 90° and 150° C. During precipitation, as more and more of the acidic salts in solution are precipitated as basic compounds, the pH of the solution gradually rises. The initial pH of the solution prior to any hydrolysis may range between about 1 and 3, and precipitation is ordinarily substantially complete when a pH level between about 6 and 7.5 is reached. It is important however not to allow the pH to rise above about 8.0, for at higher pH's soluble ammonia complexes of the divalent metal compounds begin to form.

Upon completion of the coprecipitation, the reaction slurry is then treated in conventional manner as by filtration, washing of the filter cake to remove soluble salts of reaction and excess precipitant, drying and calcining. Prior to calcination, it is normally desirable to shape the partially dried coprecipitate into the form desired, as by extrusion, pelleting, casting or the like. Final calcination may be carried out at temperatures between about 700° and 1,200° F. for periods ranging between 1–12 hours or more. The calcined composite ordinarily has a total surface area ranging between about 30 and 200 m$^2$/g, and an active metal surface area (after hydrogen reduction) ranging between about 2 m$^2$/g (for catalysts of low active metal content) up to about 18 m$^2$/g (for catalysts having a relatively high active metal content).

It is to be understood that when referring to the divalent metals employed herein, such divalency need exist only in the salt or salts as precipitated; after precipitation, calcination in air, or hydrogen reduction, the formerly divalent metal may be present at either higher or lower valencies.

According to one modification of the invention, a dried coprecipitate produced as described above may be admixed with an alumina hydrogel or hydrosol in order to provide a binder for improving pellet strength. It has been found moreover that this procedure not only improves pellet strength but also still further improves the thermal stability of the catalyst, up to temperatures of at least about 1,500° F. For purposes of providing pellet strength, only about 10–25 weight percent of alumina binder is required, but amounts up to about 80–90% may be utilized to prepare catalysts of higher thermal stability for use in reactions such as high temperature methanation in the range of about 1,000°–1,500° F., which are mass transfer limited. Such mass transfer limitations also render the diluted catalysts useful at lower methanation temperatures in the range of about 600°–1000° F. Dilution of the catalyst with a porous alumina matrix assists in overcoming diffusion limitations, giving a more efficient utilization of the surface area of the active metal component.

However, the above dilution technique does not give the maximum possible stability for a given active metal content. A far greater improvement in high-temperature stability is obtained by coprecipitating most or all of the alumina along with the active metal, so that the final composition contains at least about 1, preferably about 1.5–20 parts by weight of coprecipitated $Al_2O_3$ per part of active metal oxide. This technique provides for greater microscopic dilution of the active metal by the alumina. High temperature thermal stability appears to be strongly correlated with the degree of separation of microscopic active metal particles in the alumina matrix. Mixing extraneous alumina with a previously coprecipitated active metal-alumina composite does not appreciably change the disposition of active metal in the original coprecipitate.

USE OF CATALYSTS

Catalysts prepared as described above are useful in a wide variety of chemical reactions carried out under reducing conditions at between about 300° and 2000° F., in which thermal stability is a problem. The nickel-containing catalysts show outstanding utility in the hydrogenation of carbon oxides (methanation) to produce methane, a reaction which is generally carried out at temperatures ranging between about 700° and 1500° F. and pressures between about 100–1,500 psig. The reaction is extremely exothermic, and much difficulty has been encountered in controlling temperature rise in the reactor. One widely used technique under adiabatic conditions involves the recycle of large volumes of product gas (mainly methane) to serve as a heat sink, thus adding greatly to operating costs.

A less expensive approach to temperature control involves conducting the methanation in two or more adiabatic stages, with intervening cooling of the reactant gases. In the first of such stages, it would be very desirable to initiate the reaction at low temperatures of e.g. 500°–700° F. and allow the exothermic temperature rise to level out at e.g. 1350°–1500° F., at which temperature equilibrium limitations substantially suppress further exothermic reaction. The exit gases are then cooled to e.g. 600°–950° F. and passed into a second stage in which more favorable equilibrium peak temperatures of e.g. 1100°–1250° F. are reached. Further completion of the reaction can be achieved in a third stage operating at inlet temperatures of e.g. 500°–650° F. and peak temperatures of e.g. 750°–850° F. At the latter temperatures, thermodynamics permit the methanation reaction to go to 95-98% completion.

Previously available methanation catalysts do not permit of taking maximum advantage of the above multi-stage operation. At any given methanation temperature, catalyst life is a problem. Some catalysts are fairly stable at the lower temperatures, but unstable at the high temperatures. No catalyst has yet been found which can maintain its activity over the wide temperature range desired in the first stage operation described above. The only known catalysts which are sufficiently stable at temperatures above about 1100°-1200° F. rapidly become inactive for low-temperature methanation, to the extent that they will not initiate the reaction at temperatures below about 1200° F. As a consequence, it has been found necessary to carry out such first-stage operations with inlet gas temperatures above 1200° F., thereby markedly decreasing efficiency.

The catalysts of this invention can easily be adapted for use in the above or other methanation processes. For maximum first-stage stability and activity over the entire temperature range of 600°-1500° F., and particularly at temperatures between about 1100° and 1500° F., it is preferred to employ catalysts containing about 5-40%, preferably about 10-30% by weight of NiO. For maximum stability and activity in subsequent stages, particularly at temperatures between about 600° and 1100° F., it is preferred to employ catalysts containing about 30-80%, preferably about 40-70% by weight of nickel, calculated as NiO.

The cobalt containing catalysts of this invention are particularly useful in the Fischer-Tropsch reaction, wherein hydrogen and carbon monoxide are reacted at temperatures in the range of about 300°-600° F. to produce paraffin hydrocarbons mainly in the $C_6$-$C_{12}$ range. They are also useful in the water-gas shift reaction wherein carbon monoxide is reacted with steam to produce hydrogen and carbon dioxide.

When modified by the addition of a minor proportion of an inhibitor such as an alkali or alkaline earth metal oxide, the iron, nickel and cobalt catalysts of this invention are also useful in the steam reforming of $C_1$-$C_6$ paraffins to produce hydrogen by the endothermic reverse of the methanation and/or Fischer-Tropsch reactions. Steam reforming is normally carried out at temperatures ranging between about 1500° and 2000° F. At lower temperatures, in the 700°-1000° F. range, these catalysts are also useful for direct steam gasification of naphthas to produce methane (an overall exothermic reaction).

In all of the foregoing processes, strong reducing conditions prevail due to the presence of CO and/or $H_2$ in combined amounts ranging between about 10% and 100% by volume. This reducing atmosphere is believed to effect a slow conversion of the divalent metal aluminates, or some other inactive divalent metal compound, to active free metal. This mechanism can replace activity gradually lost through metal agglomeration or through sulfur poisoning.

The following examples are cited to illustrate the invention, but are not to be construed as limiting in scope:

EXAMPLE I

A solution of 244 grams of $Ni(NO_3)_2.6H_2O$, plus 1350 grams of $Al(NO_3)_3.9H_2O$ plus 375 grams of urea was prepared in 3000 ml $H_2O$. This was placed in an oven at 95° C. until precipitation was reached at a pH of 6.4 (approximately 40 hours). The entire product was dried at 220° F., then washed three times with 1000 ml $H_2O$ and redried. The dried product was pulverized through a 100-mesh screen, mulled with peptized alumina gel containing 57 grams of $Al_2O_3$ (20% by weight of calcined final product), and extruded through a 1/16 inch die. The product was air-dried overnight, and calcined at 900° F. for 2 hours. The finished catalyst analyzed 20.8% NiO, and had a surface area of 201 $m^2/g$.

EXAMPLE II

A high-nickel catalyst was prepared as follows: About 8730 grams of $Ni(NO_3)_2.6H_2O$ was dissolved in 15,000 ml $H_2O$, and 11,250 grams of $Al(NO_3)_3.9H_2O$ was dissolved in 12,000 ml $H_2O$ to which another 3000 ml of $H_2O$ was added after mixing the two salt solutions in a 25-gallon steam-jacketed stainless-steel kettle equipped with stirrer and thermometer. A third solution consisting of 4800 grams of urea in 15,000 ml $H_2O$ was then added to the kettle. The total volume of solution in the kettle was about 15.4 gallons.

The solution was heated by introducing 15-pound steam into the kettle jacket. Vigorous stirring was used to obtain rapid heat transfer; heat-up to 209° F. required about 1 hour. At this temperature, rapid evolution of $CO_2$ occurred due to urea hydrolysis. After about four hours at 209°-210° F. the pH had risen from about 2.3 to 4.5, at which point some precipitation had started. A sample of initial precipitate was taken for analysis. It contained 74.4% NiO and 25.0% $Al_2O_3$ after calcining at 900° F.

By X-ray diffraction analysis of the oven-dried (110° C.) precipitate before calcination, a pattern was obtained indicating the presence of 50 Å crystallites of a material very similar, but not identical, to basic nickel carbonate ($NiCO_3.2Ni(OH)_2.4H_2O$). Thus, a nickel component was precipitating at a pH of 4.5 along with aluminum hydroxide.

Urea hydrolysis was allowed to continue, the pH rising to 5.3 in 85 more minutes where it remained for about 2 hours before slowly rising to about 6.0 during the next 2.5 hours. The slurry was then allowed to cool overnight before discharge from the kettle and filtering.

A sample of filtrate was analyzed for nickel by X-ray fluorescence and found to contain 3.6 mg Ni/ml. Since a total of 29 liters of filtrate was collected, 104.4 grams of nickel out of 1760 grams taken had not precipitated, or about 6% of the total. A sample of filtrate was heated at 95° C. for another 24 hours and further precipitation occurred. This precipitate was of almost the same composition as that of the initial precipitate — 70.1% NiO and 29.9% $Al_2O_3$ after calcination at 900° F. This shows that loss of nickel can be substantially eliminated by longer digestion time or by using slightly more urea, so that the final pH is close to 7 (but below about pH 8, where soluble ammonia complexes begin to form).

After a final water wash, the filter cake was dried at 250° F. to an LOI of 32.2%. It was ground to a fine powder in a hammer mill, dry-ground in a muller for 2 hours, then wet-mulled to an extrudable paste. The paste was then extruded through a 1/16 inch die, air dried, and calcined at 900° F. for 3 hours. The finished catalyst contained 55.9% NiO and had a total surface area of 184 $m^2/g$.

After reducing for 16 hours at 700° F. in 100% $H_2$ as disclosed in J.A.C.S. 86 p.2996 (1964), the catalyst was found to have a nickel surface area of 8.3 $m^2/g$. as measured by the Flow method described in *J. Catalysis*, 9, p.125 (1967). By the Pulse Chromatographic Method described in *J. Gas Chromatography*, 6, p. 161 (1968), a nickel surface area of 13.4 m²/g was indicated after the catalyst had been reduced at 842° F. for 4 hours and desorbed in nitrogen for 16 hours before cooling to 212° F. for the hydrogen adsorption measurement. This apparent resistance toward reduction is an indication of the intimate combination of nickel with the alumina component.

EXAMPLE III

Aluminum hydroxide and nickel hydroxide were prepared separately by homogeneous precipitation with urea from separate solutions of $Ni(NO_3)_2.6H_2$ in $H_2O$ and of $Al(NO_3)_3.9H_2O$ in water. The final pH of precipitation of the nickel component was about 7.0 and about 6.4 for the alumina component. Each precipitate was dried separately and washed to remove $NH_4NO_3$. Then each preparation was dried and pulverized through a 100-mesh screen. Enough of the precipitated nickel component was blended with the dried alumina component to give a final product containing about 21% NiO (same as in Example I). The blend was mulled without additional binder and extruded through a 1/16 inch die. After air drying overnight, the extrudate was calcined for 2 hours at 900° F. The finished catalyst contained 21.4% NiO and had a surface area of 58 m²/g. The surface area of a pelleted sample of the alumina component was only 36 m²/g. Thus, coprecipitation with nickel, as in Example I, apparently stabilizes the alumina surface area.

EXAMPLE IV

The foregoing catalysts, along with two commercial methanation catalysts, were tested for thermal stability in a special high-temperature test. The conditions of the test were as follows:

| Feed Gas Composition: | |
|---|---|
| $H_2$ | 30.9 vol.% |
| $CH_4$ | 9.6 |
| CO | 7.9 |
| $CO_2$ | 7.9 |
| $H_2O$ | 43.7 |
| Inlet Temperature | 900° F |
| Outlet Temperature | 1220° F (Calculated Adiabatic) |
| Pressure | 300 psig |
| Catalyst Volume | 85 ml (13" bed length) |
| GHSV | 10,000 |

Since the reactor was heated in a fluidized sand bath, reaction conditions were not adiabatic, but quasi-isothermal. Typically, the peak temperatures were 1150°–1175° F., dropping to about 925° F. at the outlet as a result of cooling by the sand bath. The equilibrium composition established at the lower temperature corresponds to approximately 98% conversion of CO.

Thermocouples were placed at less than one-inch intervals in the catalyst bed and the temperature profile recorded as a function of time. As the catalysts deactivate, the peak temperature travels slowly down the bed and is picked up by successive thermocouples. The rate of deactivation is simply the number of days required for peak to travel 1 inch. The greater the number of days required, the greater is the thermal stability of the catalyst. The results of the tests were as follows:

TABLE I

| Catalyst | Method of Preparation | Wt.% NiO | Deactivation Rate, Days/Inch |
|---|---|---|---|
| Example I | Homogeneous Coprecipitation | 20.8 | 8.7 |
| Example II | Homogeneous Coprecipitation | 55.9 | 190 |
| Example III | Separate Homogeneous Precipitation | 21.4 | 2.3 |
| Commercial[1] | Non-Homogeneous Coprecipitation | <50 | 6.2 |
| Commercial[2] | | <50 | 0.9 |

It is apparent that the catalyst of Example II is vastly superior to the remaining catalysts. Further, it is apparent that the Ni/Al ratio in the coprecipitate is a very significant factor. For practical purposes, the NiO content should be at least about 30 weight-percent.

EXAMPLE V

This Example demonstrates that the foregoing results are not obtainable with catalysts prepared by the non-homogeneous coprecipitation method described in U.S. Pat. No. 3,320,182, even though the precipitating anions are the same as in the foregoing examples.

About 350 grams of $Ni(NO_3)_2.6H_2O$ and 450 grams of $Al(NO_3)_3.9H_2O$ were dissolved in 1800 ml $H_2O$. The solution was heated to 95° C. and then, little by little, 413 grams of powdered $NH_4HCO_3$ was added with constant stirring, while maintaining the temperature at 95° C. Approximately 105 minutes were required to add the precipitant slowly enough to avoid loss by foaming. Periodic additions of hot water were made to make up evaporation losses.

A second preparation was made exactly as the above, except the addition time of $NH_4HCO_3$ was 80 minutes (pushing the reaction to just short of overflow by foaming), and 425 grams thereof were added. The final pH in the two cases was 6.1 and 5.9, respectively, making an average of 6.0. The two batches were combined after filtration, dried at 250° F. overnight and washed to remove excess nitrate. The washed product was then dried again at 250° F., mulled to an extrudable paste with water, and extruded through a 1/16 inch die. The extrudate was then dried at 250° F. and calcined at 900° F. for 3 hours. The final catalyst had a NiO content of 60.2% by weight (47.3% Ni) and a surface area of 200 m²/g.

When tested by the procedure described above, the deactivation rate was found to be 113 days/inch versus 190 days/inch for the catalyst of Example II. It is thus clear that coprecipitation of nickel and alumina from homogeneous solution by urea hydrolysis gives a distinctly more stable catalyst (68% more stable in this comparison) than does non-homogeneous coprecipitation by addition of $NH_4HCO_3$.

The following Examples VI–IX show the effect of varying NiO content, and the ratio of coprecipitated $Al_2O_3$ to NiO on stability at different methanation temperatures.

EXAMPLE VI

A coprecipitated nickel-alumina catalyst was prepared by the urea hydrolysis method as follows:

A solution was prepared by dissolving 244 grams of $Ni(NO_3)_2.6H_2O$ and 1350 grams of $Al(NO_3)_3.9H_2O$ in 300 ml of water. To this solution was added 375 grams of crystalline urea and the mixture was heated to about 60° C. Then it was placed in a preheated oven at 90°–95°

C. and held at this temperature level until the pH reached 6.4. The resulting gel was dried and then washed with 3 one-liter batches of water and redried. The product was ground to pass a 100-mesh screen and mulled with enough peptized alumina gel to add 20% of additional $Al_2O_3$ to the composite (anhydrous basis). The paste was then extruded through a 1/16 inch die, dried, and calcined at 900° F. for 2 hours. The finished catalyst contained 20.8% NiO and had a total surface area of 201 $m^2/g$. The catalyst was tested as 1/16 inch extrudate as described in Example IX.

EXAMPLE VII

A semi-commercial batch of a nickel-alumina coprecipitate was prepared essentially as described in Example VI but with a nominal composition of 60% NiO. 40% $Al_2O_3$. A 158 gram sample of this preparation (100 g. of $60NiO.40Al_2O_3$ anhydrous) was pulverized to a fine powder and mixed with 268 grams of alumina hydrate (200 g. anhydrous $Al_2O_3$). This was pelleted with 2% graphite into 3/16 inch × 3/16 inch tablets and calcined at 900° F. for 1 hour. The finished catalyst had a total surface area of 228 $m^2/g$ and a NiO content of 20.0%. The catalyst was granulated to pass through a 12-mesh screen and retained on a 14-mesh screen (U.S. Sieve) for testing.

EXAMPLE VIII

Another sample of the 60% NiO. 40% $Al_2O_3$ coprecipitate from Example VII was pulverized and admixed with only sufficient alumina hydrate to provide a total of 52% $Al_2O_3$ in the finished catalyst (20% added $Al_2O_3$). The resulting product was worked up and granulated as in Example VII. It contained 48 wt.% NiO.

EXAMPLE IX

The catalysts of Examples VI–VIII were tested by two procedures, one the standard test described in Example IV and the other a high temperature test. The test conditions were as follows:

TABLE 2

| | Standard | High Temperature |
|---|---|---|
| GHSV, volume/volume cat. | 10,000 | 10,000 |
| Pressure, psig | 300 | 300 |
| Inlet Temp., ° F | 900 | 1300 |
| Peak Temp., ° F | 1165 | 1424 |
| Feed Gas Composition, Mol % | | |
| CO | 7.9 | 22.5 |
| $H_2$ | 30.9 | 22.5 |
| $CO_2$ | 7.9 | 0.0 |
| $CH_4$ | 9.6 | 0.0 |
| $H_2O$ | 43.7 | 55.0 |

The results of the tests were as follows:

TABLE 3

| Catalyst | Wt.% NiO | Parts Coppt'd $Al_2O_3$/part NiO | Deactivation Rate,Days/Inch 900° F Inlet | 1300° F Inlet |
|---|---|---|---|---|
| Ex. VI | 20.8 | 2.85 | 8.7 | 400 |
| Ex. VII | 20 | 0.66 | 8.0 | 42 |
| Ex. VIII | 48 | 0.66 | 124 | 64 |

It is clear that at the lower inlet temperature (~1165° F. peak temperature), stability is a function of total nickel content. However, at the higher inlet temperature (~1425° F. peak temperature) there is very little correlation with total nickel content, but a strong correlation with the extent of dilution of nickel with coprecipitated $Al_2O_3$. That is to say, the high temperature stability is vastly improved by greater separation of the microscopic nickel particles in the initial coprecipitation process.

EXAMPLE X

Preparation of 60 CoO.40 $Al_2O_3$

A homogeneous solution of a cobalt salt, an aluminum salt, and urea was prepared by dissolving 436.5 grams (1.5 moles) of $Co(NO_3)_2.6H_2O$, 562.5 grams (1.5 moles) of $Al(NO_3)_3.9H_2O$, and 240 grams (4 moles) of crystalline urea in 1688 ml of distilled water. The solution was placed in a 3-liter flask equipped with stirrer, condenser, and thermometer, heated to boiling and held there until the pH reached 5.9.

The slurry was then filtered, washed by reslurrying and refiltering three times, and finally washed once on the filter. The product was dried and calcined at 900° F. The calcined powder analyzed 55.0% CoO and had a total surface area of 129 $m^2/g$.

As in the case of the nickel analogue, this highly dispersed cobalt catalyst has exceptional thermal stability which makes it particularly useful in exothermic reactions such as the Fischer-Tropsch reaction:

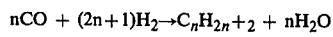

$$nCO + (2n+1)H_2 \rightarrow C_nH_{2n+2} + nH_2O$$

or the water-gas shift reaction:

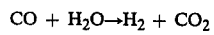

$$CO + H_2O \rightarrow H_2 + CO_2$$

At lower cobalt levels it makes a particularly useful base for molybdenum or tungsten oxides and/or sulfides for hydrotreating (hydrodesulfurization) catalysts. In general, it is useful in a wide variety of hydrogenation reactions.

The following claims and their obvious equivalents are intended to define the true scope of the invention.

I claim:

1. In a process wherein a chemical conversion is carried out by contacting at least one fluid reactant with a solid catalyst under reducing conditions in the presence of hydrogen and/or carbon monoxide, and at temperatures between about 300° and 2000° F. to produce a product chemically different from said reactant, said catalyst consisting essentially of a composite of alumina and one or more iron group metals, and wherein progressive thermal deactivation of said catalyst takes place, the improvement which comprises using as said catalyst a composite of improved thermal stability prepared by the steps of:

(1) forming at a relatively low temperature a homogeneous aqueous solution of an aluminum salt, a salt or salts of at least one divalent iron group metal and a delayed precipitant, said delayed precipitant being a water-soluble compound which, at said relatively low temperature, does not bring about precipitation of the metal salts dissolved in said solution, but which will hydrolyze at a relatively higher temperature to form ammonia and carbon dioxide;

(2) heating said aqueous solution to a sufficiently high temperature and for a sufficient time to bring about hydrolysis of said delayed precipitant with resultant gradual increase in pH of said solution and formation of a homogeneous coprecipitate of basic compounds of aluminum and of the divalent metal content of said solution;

(3) separating said coprecipitate from said solution before the latter reaches a pH above about 8; and (4) drying and calcining said coprecipitate.

2. A chemical conversion as defined in claim 1 wherein said delayed precipitant is urea.

3. A chemical conversion as defined in claim 2 wherein said catalyst comprises between about 20–95 weight-percent alumina and about 5–80 weight-percent of said iron group metal component calculated as divalent metal oxide.

4. A chemical conversion as defined in claim 3 wherein said iron group metal is nickel.

5. A chemical conversion as defined in claim 3 wherein said iron group metal is cobalt.

6. A chemical conversion as defined in claim 3 wherein said iron group metal is iron.

7. A process for the hydrogenation of carbon oxides to produce methane, which comprises contacting a feed gas comprising hydrogen and an oxide of carbon with a nickel-alumina catalyst at a temperature between about 600° and 1500° F., and recovering from said contacting a methane-enriched product gas, said catalyst having been prepared by the steps of:

(1) forming at a relatively low temperature a homogeneous aqueous solution of an aluminum salt, a nickel salt, and a delayed precipitant, said delayed precipitant being a water-soluble compound which, at said relatively low temperature, does not bring abut any significant precipitation of the metal salts dissolved in said solution, but which will hydrolyze at a relatively higher temperature to form ammonia and carbon dioxide;

(2) heating said aqueous solution to a sufficiently high temperature and for a sufficient time to bring about hydrolysis of said delayed precipitant with resultant gradual increase in pH of said solution and formation of a homogeneous coprecipitate of basic compounds of alumina and nickel;

(3) separating said coprecipitate from said solution before the latter reaches a pH above about 8; and (4) drying and calcining said coprecipitate.

8. A process as defined in claim 7 wherein said delayed precipitant is urea.

9. A process as defined in claim 7 wherein said catalyst comprises between about 20–95 weight-percent alumina and about 5–80 weight-percent of nickel calculated as NiO.

10. A process as defined in claim 9 wherein said contacting is carried out at between about 800° and 1200° F.

11. A process as defined in claim 7 wherein said catalyst comprises between about 30–85% by weight of alumina, and about 15–70% by weight of nickel calculated as NiO, and wherein said delayed precipitant is urea.

12. A process as defined in claim 11 wherein said contacting is carried out at between about 800° and 1200° F.

13. A process for the hydrogenation of carbon oxides to produce methane, which comprises contacting a feed gas comprising hydrogen and carbon monoxide with a nickel-alumina catalyst at a temperature between about 600° and 1500° F., and recovering from said contacting a methane-enriched product gas, said catalyst having been prepared by the steps of:

(1) forming at a relatively low temperature, a homogeneous aqueous solution of an aluminum salt, a nickel salt, and a delayed precipitant, said delayed precipitant being a water-soluble compound which, at said relatively low temperature does not raise the pH of said solution above about 4.0, but which will hydrolyze at a relatively higher temperature to form ammonia and carbon dioxide, the proportion of said delayed precipitant employed being at least sufficient to generate by hydrolysis an amount of ammonia stoichiometrically sufficient to convert all metal salts in solution to their hydroxides;

(2) heating said solution to bring about a sufficient hydrolysis of said delayed precipitant to raise the pH of said solution to between about 6 and 7.5, with resultant substantially complete coprecipitation of the metal salts in said solution as hydroxides and/or other basic compounds; and (3) recovering, drying and calcining the resulting coprecipitate.

14. A process as defined in claim 13 wherein said delayed precipitant is urea.

15. A process as defined in claim 14 wherein said contacting is carried out at a temperature between about 600° and 1100° F., and said catalyst comprises between about 30–60 weight-percent alumina and about 40–70 weight-percent of nickel calculated as NiO.

16. A process as defined in claim 14 wherein said contacting is carried out at least in part at temperatures between about 1100° and 1500° F., and said catalyst comprises between about 70–90% by weight of alumina, and about 10–30% by weight of nickel calculated as NiO, and wherein said delayed precipitant is urea.

* * * * *